US010932418B2

(12) United States Patent
Millar et al.

(10) Patent No.: US 10,932,418 B2
(45) Date of Patent: Mar. 2, 2021

(54) SYSTEMS AND METHODS FOR UTILIZING WAVES IN AN ASSEMBLY LINE GROW POD

(71) Applicant: Grow Solutions Tech LLC, Lehi, UT (US)

(72) Inventors: Gary Bret Millar, Highland, UT (US); Mark Gerald Stott, Eagle Mountain, UT (US); Todd Garrett Tueller, American Fork, UT (US)

(73) Assignee: Grow Solutions Tech LLC, Vineyard, UT (US)

( * ) Notice: Subject to any disclaimer, the term of this patent is extended or adjusted under 35 U.S.C. 154(b) by 350 days.

(21) Appl. No.: 15/987,306

(22) Filed: May 23, 2018

(65) Prior Publication Data

US 2018/0359930 A1 Dec. 20, 2018

Related U.S. Application Data

(60) Provisional application No. 62/519,647, filed on Jun. 14, 2017.

(51) Int. Cl.
*A01G 7/04* (2006.01)
*A01G 7/00* (2006.01)
(Continued)

(52) U.S. Cl.
CPC ........... *A01G 7/00* (2013.01); *A01G 7/04* (2013.01); *A01G 31/042* (2013.01); *A01G 31/06* (2013.01);
(Continued)

(58) Field of Classification Search
CPC ...................................................... A01G 7/04
(Continued)

(56) References Cited

U.S. PATENT DOCUMENTS 5,860,248 A * 1/1999 Peters .................... A47G 7/047
47/66.6
7,600,343 B2 * 10/2009 Schultheiss .............. A01G 7/04
47/58.1 LS
(Continued)

FOREIGN PATENT DOCUMENTS

GB 2121263 A 12/1983
KR 100971702 B1 7/2010
(Continued)

OTHER PUBLICATIONS

"Biowave Mini Growth Booster," https://www.webhydroponics.com/shop/biowave-mini/ (accessed Mar. 29, 2018.
(Continued)

*Primary Examiner* — David J Parsley
(74) *Attorney, Agent, or Firm* — Dinsmore & Shohl LLP (57) ABSTRACT

A system for utilizing waves in an assembly line grow pod includes a plurality of carts, a wave generator and a master controller. The plurality of carts carries a plurality of plants including a first plant and a second plant. The wave generator generates sound waves having a different range of frequency. The master controller is communicatively coupled to the wave generator and comprising a processor and a memory storing a wave recipe and instructions. The wave recipe correlates the plurality of plants with different characteristics of sound waves including frequency. The wave generator generates a first sound wave having the characteristic correlated to the first plant and a second sound wave having the characteristic correlated to the second plant.

20 Claims, 5 Drawing Sheets

(51) Int. Cl.
  *A01G 31/06* (2006.01)
  *A01G 31/04* (2006.01)
  *G10K 15/02* (2006.01)
  *G01N 33/00* (2006.01)
  *G05B 15/02* (2006.01)
  *G10K 15/04* (2006.01)
(52) U.S. Cl.
  CPC ......... *G01N 33/0098* (2013.01); *G05B 15/02* (2013.01); *G10K 15/02* (2013.01); *G10K 15/04* (2013.01)
(58) Field of Classification Search
  USPC .................................. 47/1.3, 58.1 R, 58.1 LS
  See application file for complete search history.

(56) References Cited

U.S. PATENT DOCUMENTS

| | | | | |
|---|---|---|---|---|
| 8,074,397 | B2* | 12/2011 | Yoneda | A01G 7/045 |
| | | | | 47/1.01 R |
| 8,701,340 | B2* | 4/2014 | Adams | A01G 7/04 |
| | | | | 47/1.01 R |
| 2007/0039389 | A1* | 2/2007 | Brooks | A61B 8/00 |
| | | | | 73/579 |
| 2014/0169138 | A1 | 6/2014 | Kim | |
| 2015/0089866 | A1 | 4/2015 | Abbott | |
| 2015/0121753 | A1* | 5/2015 | Jenner | A01G 7/045 |
| | | | | 47/58.1 LS |

FOREIGN PATENT DOCUMENTS

| | | |
|---|---|---|
| KR | 20120017487 A | 2/2012 |
| KR | 101296842 B1 | 8/2013 |
| KR | 20150069756 A | 6/2015 |
| KR | 20150069757 A | 6/2015 |
| WO | 90/13996 A1 | 11/1990 |
| WO | 98/49283 A1 | 11/1998 |
| WO | 2013/066254 A1 | 5/2013 |

OTHER PUBLICATIONS

International Search Report and Written Opinion for PCT/US2018/034590 dated Oct. 2, 2018, 15 pages.

* cited by examiner

SYSTEMS AND METHODS FOR UTILIZING WAVES IN AN ASSEMBLY LINE GROW POD

CROSS REFERENCE

This application claims the benefit of U.S. Provisional Application Ser. No. 62/519,647, filed on Jun. 14, 2017, which is incorporated by reference in its entirety.

TECHNICAL FIELD

Embodiments described herein generally relate to systems and methods for utilizing waves in a grow pod and, more specifically, to providing waves to plants in moving carts based on a wave recipe for the plants.

BACKGROUND

While crop growth technologies have advanced over the years, there are still, many problems in the farming and crop industry today. As an example, while technological advances have increased efficiency and production of various crops, many factors may affect a harvest, such as weather, disease, infestation, and the like. Additionally, while the United States currently has suitable farmland to adequately provide food for the U.S. population, other countries and future populations may not have enough farmland to provide the appropriate amount of food. Accordingly, there is a need to provide an organized plant grow pod system which facilitates a quick growing, small footprint, chemical free, low labor solution to growing microgreens and other plants for harvesting. At the same time, there is a need that the organized plant grow pod system may provide controlled and optimal environmental conditions (e.g., the timing and wavelength of light, pressure, temperature, watering, nutrients, molecular atmosphere, and/or other variables) in order to maximize plant growth and output. In particular, it is important to ensure that plants or seeds will be provided with favorable growth conditions, which would have significantly promoted plant growth and output.

SUMMARY

Systems and methods for utilizing waves in an assembly line grow pod are described. One embodiment of a method includes a method for utilizing waves in an assembly line grow pod includes (i) arranging a plurality of plants having a first plant and a second plant on a plurality of carts; (ii) identifying the first plant carried on one or more carts; (iii) identifying the second plant carried on one or more carts; (iv) storing, in a memory, a wave recipe that correlates the plants on the carts with different characteristics of sound waves; (v) upon identification of the first plant, retrieving from the wave recipe a characteristic of a sound wave correlated to the first plant; (vi) upon identification of the second plant, retrieving from the wave recipe a characteristic of a sound wave correlated to the second plant; (v) generating, with a wave generator, a first sound wave having the characteristic correlated to the first plant; and (vii) generating, with the wave generator, a second sound wave having the characteristic correlated to the second plant.

In another embodiment, a method for utilizing waves in an assembly line grow pod, includes (i) arranging a plurality of plants having a first plant and a second plant on a plurality of carts; (ii) arranging a master controller having a memory and a processor; (iii) storing, in the memory, a wave recipe that correlates the plants on the carts with a characteristic of sound waves; (iv) controlling, with the master controller, a wave generator to generate sound waves having different characteristics based on the wave recipe; (v) identifying, with the master controller, the first plant carried on the carts; (vi) identifying, with the master controller, the second plant carried on the carts; (vii) upon identification of the first plant, retrieving from the wave recipe the characteristic of the sound waves correlated to the first plant; (viii) upon identification of the second plant, retrieving from the wave recipe the characteristic of the sound waves correlated to the second plant; (ix) generating, with the wave generator, a first sound wave having the characteristic correlated to the first plant; and (ix) generating, with the wave generator, a second sound wave having the characteristic correlated to the second plant.

In yet another embodiment, a system for utilizing waves in an assembly line grow pod, includes a plurality of carts, a wave generator, and a master controller. The plurality of carts carries a plurality of plants including a first plant and a second plant. The wave generator generates sound waves having a different range of a frequency. The master controller is communicatively coupled to the wave generator and includes a processor and a memory storing a wave recipe and instructions. The wave recipe correlates the plurality of plants with different characteristics of sound waves. The instructions, upon execution by the processor, perform operations including (i) identifying the first plant carried on the carts; (ii) identifying the second plant carried on the carts; (iii) retrieving from the wave recipe each characteristic of the sound waves of the first plant and the second plant, respectively; (iv) causing the wave generator to generate a first sound wave having the characteristic correlated to the first plant; and (v) causing the wave generator to generate a second sound wave having the characteristic correlated to the second plant.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Embodiments disclosed herein include systems and methods for utilizing waves in a grow pod. Some embodiments are configured with a grow pod that includes a rail system, carts moving along the rail system, a wave generator configured to generate waves, and a master controller. The master controller identifies plants in the carts, retrieves wave recipes based on the identified plants, and instructs the wave generator to generate the waves at certain frequencies based on the wave recipes. The wave recipes include frequencies of ultrasound and frequencies of audible sound. The systems and methods for utilizing waves in a grow pod incorporating the same will be described in more detail, below.

Figure 1:
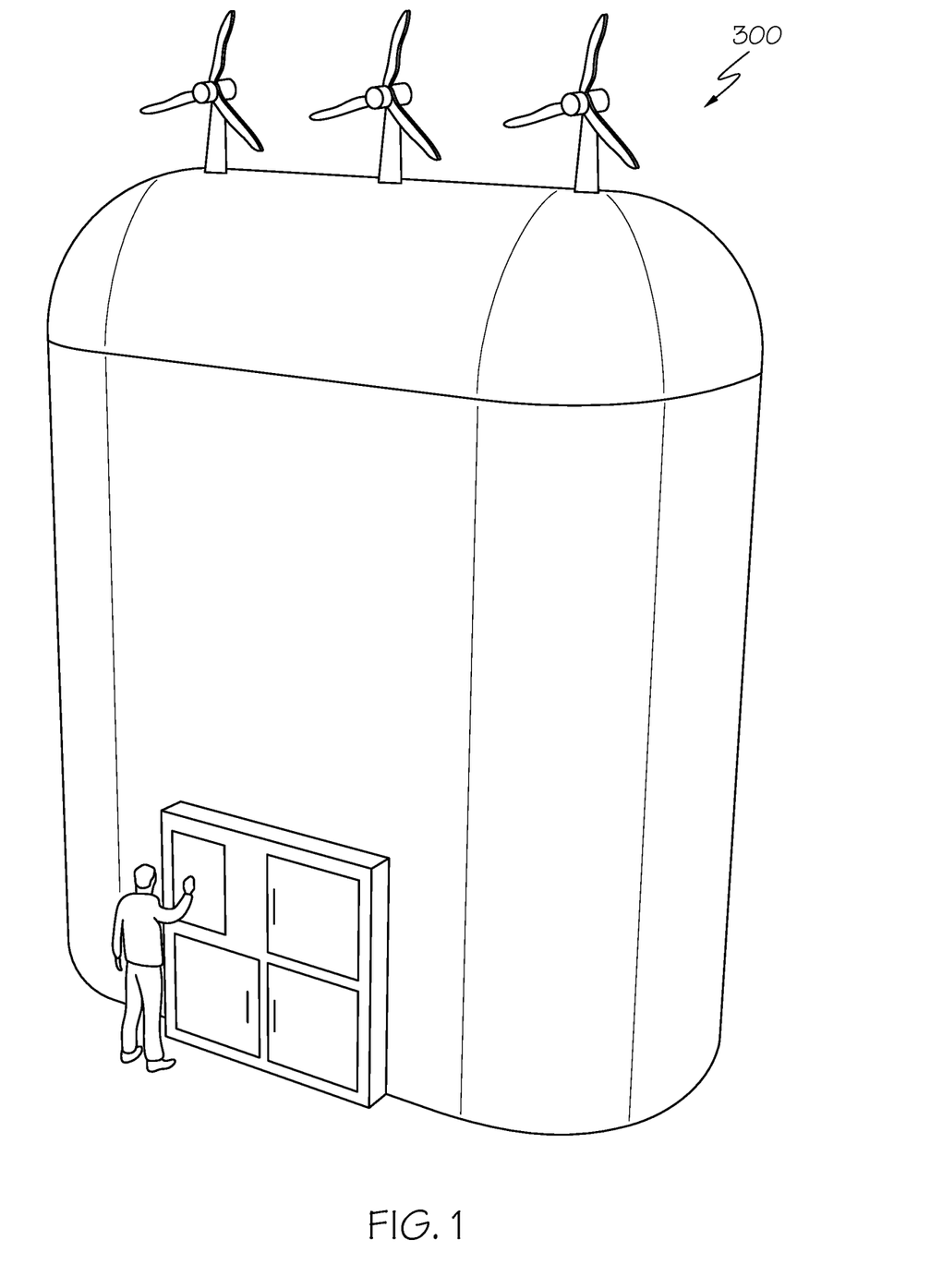
FIG. 1 depicts an exterior enclosure for an assembly line grow pod, according to embodiments described herein.

Referring now to FIG. 1 depicts an exterior enclosure 300 for an assembly line grow pod, according to embodiments described herein. As illustrated, the assembly line grow pod (not shown) may be fully enclosed by the exterior enclosure 300. Depending on the embodiment, the exterior enclosure 300 may provide a pressurized environment to prevent (or at least reduce) insects, mold, and/or other organisms from entering the exterior enclosure 300. The exterior enclosure 300 also keeps the assembly line grow pod at a certain air pressure level.

As shown in FIG. 1, the exterior enclosure 300 includes a control panel at the front side thereof. A user may access the control panel to adjust settings, provide an input, and monitor the conditions, such as pressure level and other environmental conditions within the exterior enclosure 300. The surface of the exterior enclosure 300 may be smooth, or corrugated. The exterior enclosure 300 may be made from air proof material, such as concrete, steel, plastic, etc. As shown in FIG. 1, the exterior enclosure 300 has curved corners which may be suitable and customized to enclose the assembly line grow pod as illustrated in FIG. 2.

Figure 2:
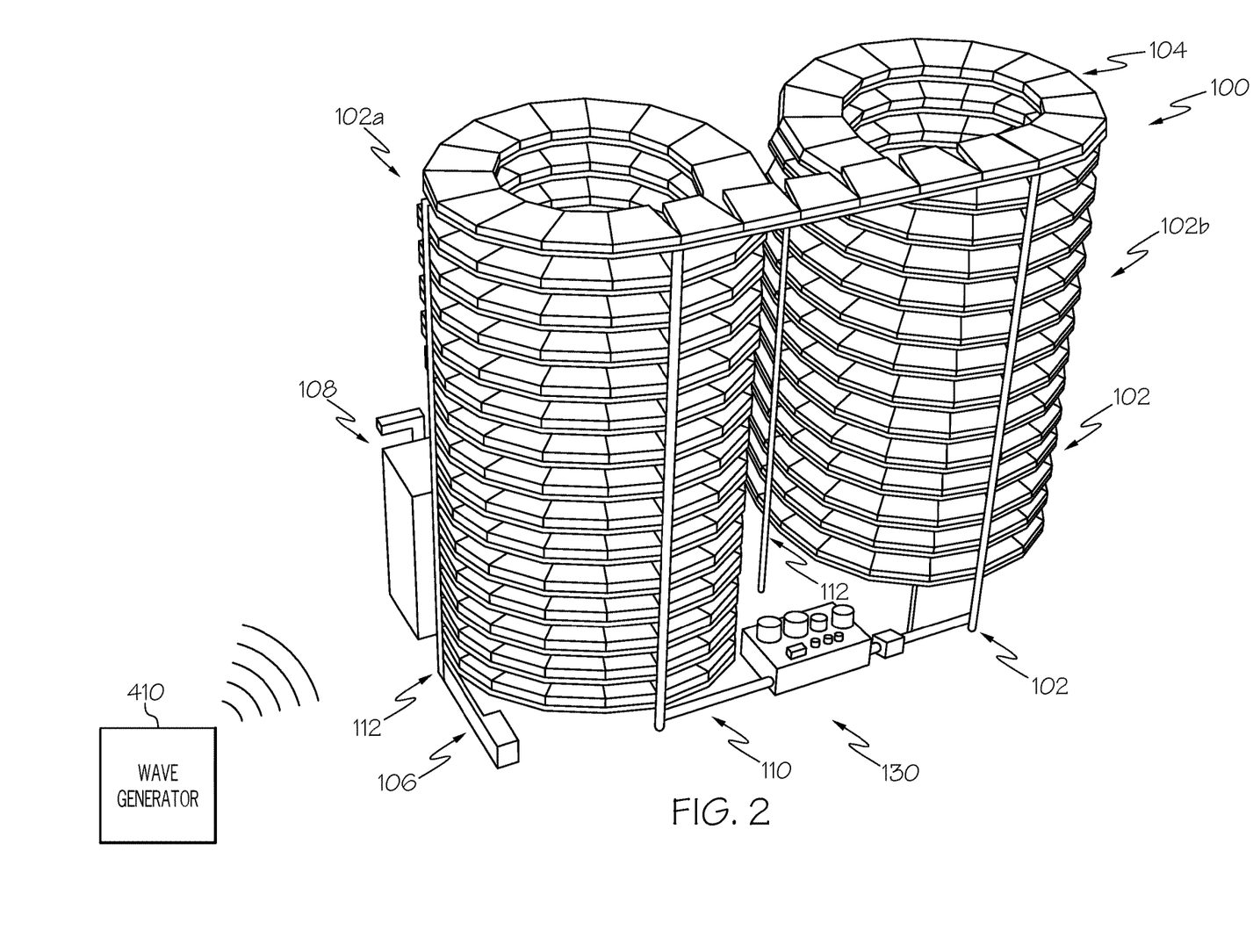
FIG. 2 depicts inside of the exterior enclosure for the grow pod, according to embodiments described herein.

Referring now to the drawings, FIG. 2 depicts an assembly line grow pod 100, according to embodiments described herein. As illustrated, the assembly line grow pod 100 may include a track 102 that holds one or more carts 104. The track 102 may include an ascending portion 102a, a descending portion 102b, and a connection portion 102c. The track 102 may wrap around (in a counterclockwise direction in FIG. 1) a first axis such that the carts 104 ascend upward in a vertical direction. The connection portion 102c may be relatively level (although this is not a requirement and is utilized to transfer carts 104 to the descending portion 102b. The descending portion 102b may be wrapped around a second axis (again in a counterclockwise direction in FIG. 2) that is substantially parallel to the first axis, such that the carts 104 may be returned closer to ground level.

While not explicitly illustrated in FIG. 2, the assembly line grow pod 100 may also include a plurality of lighting devices, such as light emitting diodes (LEDs). The lighting devices may be disposed on the track 102 opposite the carts 104, such that the lighting devices direct light waves to the carts 104 on the portion the track 102 directly below. In some embodiments, the lighting devices are configured to create a plurality of different colors and/or wavelengths of light, depending on the application, the type of plant being grown, and/or other factors. While in some embodiments, LEDs are utilized for this purpose, this is not a requirement. Any lighting device that produces low heat and provides the desired functionality may be utilized.

Also depicted in FIG. 2 is a master controller 106. The master controller 106 may include a computing device and various control modules for controlling various components of the assembly line grow pod 100 such as a nutrient dosing control module, a water distribution control module, etc. As an example, control modules for controlling a water distribution control module, a nutrient distribution control module, an air distribution control module, etc. may be included as part of the master controller 106 which may provide a modular control interface. The modular control interface of the master controller 106 enables removal, replacement, upgrade and expansion of each control module without changing or affecting the operations of other control modules, or shutting down the master controller 106 or other components of the assembly line grow pod 100.

In some embodiments, the master controller 106 may store a master recipe for plants that may dictate the timing and wavelength of light, pressure, temperature, watering, nutrients, molecular atmosphere, and/or other variables the optimize plant growth and output. For example, the master recipe dictates lighting requirements on the third day of a particular plant at the assembly line grow pod 100, different lighting requirements on the fourth day of the plant, etc. As another example, the master recipe dictates watering needs, nutrient feeds, etc. directed to plants carried on the carts at particular locations for a particular day counted from the date that plants are introduced into the assembly line grow pod 100. The master recipe is specific, extensive and customized to cover plants supported by the assembly line grow pod 100. By way of example only, the recipe may have instructions to assist 1500 carts simultaneously operating in the assembly line grow pod 100 and carrying diverse population of plants. In some embodiments, the master controller 106 may store a wave recipe that dictates the characteristics and timing of sound waves. As discussed in detail below, sound waves may be generated and provided to plants to maximize growth of plants. Depending on plants, sound waves having different characteristics, such as different frequency, different wavelength, audible, ultrasonic, etc. may be preferred. The wave recipe correlates plants and corresponding characteristics such that upon identification of plants, corresponding wave characteristics may be retrieved and processed. In other embodiments, other specific recipes such as a watering recipe, a nutrient recipe, a dosage recipe, a temperature recipe, a pressure recipe, etc. may be available.

In some embodiments, the master recipe and the wave recipe may take any form of a structured set of data, a database, etc. such that data is organized into rows, columns, and table. Additionally, or alternatively, the master recipe and the wave recipe may be structured to facilitate the storage, retrieval, modification, addition, and deletion of data through data processing operations.

In some embodiments, the master controller 106 reads information from the master recipe and adjust the information based on known locations of plants at the assembly line grow pod 100. For example, the master controller 106 may identify the plants location based on a cart identifier which is indicative of the growth stage of the plants in the assembly line grow pod 100. Once plants enter into the assembly line grow pod 100, plants move along the spiral tracks from the ascending side to the descending side until plants arrive at the harvest stage. Thus, the location of the carts carrying plants may indicate the growth stage of plants at the assembly line grow pod 100. Then, the master controller 106 may apply the master recipe relevant to the stage of the plants, such as lighting, watering, pressure, and/or wave requirements, specific to plants growing on the fourth day at the assembly line grow pod 100.

The master controller 106 processes the master recipe and controls various components of the assembly line grow pod 100. To reduce the processing load, for example, processing the master recipe and all related events for a a large number of simultaneously operating carts carrying the diverse population of plants, the master controller 106 may distribute different and specific functions to several control modules, such as a valve controller, a dosage controller, a pump controller, etc. These control modules work autonomously, complete task(s) and report to the master controller 106. In some embodiments, the control modules may be configured as hardware modules with their own set of instructions in order to improve stability and avoid pushed updates and modifications. In other embodiments, other configurations of the control modules are available.

Coupled to the master controller 106 is a seeder component 108, as shown in FIG. 2. The seeder component 108 may be configured to seed one or more carts 104 as the carts 101 pass the seeder in the assembly line. Depending on the particular embodiment, each cart 104 may include a single section tray for receiving a plurality of seeds. Some embodiments may include a multiple section tray for receiving individual seeds in each section (or cell). In the embodiments with a single section tray, the seeder component 108 may detect presence of the respective cart 104 and may begin laying seed across an area of the single section tray. The seed may be laid out according to a desired depth of seed, a desired number of seeds, a desired surface area of seeds, and/or according to other criteria. In some embodiments, the seeds may be pre-treated with nutrients and/or anti-buoyancy agents (such as water) as these embodiments may not utilize soil to grow the seeds and thus might need to be submerged.

In the embodiments where a multiple section tray is utilized with one or more of the carts 104, the seeder component 108 may be configured to individually insert seeds into one or more of the sections of the tray. Again, the seeds may be distributed on the tray (or into individual cells) according to a desired number of seeds, a desired area the seeds should cover, a desired depth of seeds, etc.

The watering component may be coupled to one or more water lines 110, which distribute water and/or nutrients to one or more trays at predetermined areas of the assembly line grow pod 100. In some embodiments, seeds may be sprayed to reduce buoyancy and then flooded. Additionally, water usage and consumption may be monitored, such that at subsequent watering stations, this data may be utilized to determine an amount of water to apply to a seed at that time.

Also depicted in FIG. 2 are airflow lines 112. Specifically, the master controller 106 may include and/or be coupled to one or more components that delivers airflow for temperature control, pressure, carbon dioxide control, oxygen control, nitrogen control, etc. Accordingly, the airflow lines 112 may distribute the airflow at predetermined areas in the assembly line grow pod 100.

Also depicted in FIG. 2 is a wave generator 410. The wave generator 410 may generate a wide frequency range of sound waves from audible sound having a frequency of 20~20,000 Hz to ultrasound having a frequency over 20,000 Hz. In some embodiments, the wave generator 410 may output two separate waves having different frequencies, e.g., audible sound and ultrasound. Similarly, some embodiments may utilize more than one wave generator 410 placed within the exterior enclosure 300, e.g., one for generating audible sound and the other for generating ultrasound. The wave generator 410 may be implemented with any wave generator available in the art as long as a wide frequency range of waves may be generated.

The wave generator 410 may be communicatively coupled to the master controller 106. In some embodiments, the wave generator 410 communicates with the master controller 106 through a wired connection. In some embodiments, the wave generator 410 includes network interface hardware such that the wave generator 410 wirelessly communicates with the master controller 106 through the network 450. The operations of the wave generator 410 may be controlled by the master controller 106. For example, the master controller 106 sends an instruction to the wave generator 410 for output waves of a certain frequency.

In some embodiments, the master controller 106 stores wave recipes for various plants. Recipes for plants such as the master recipe may dictate the timing and wavelength of light, pressure, temperature, watering, nutrients, molecular atmosphere, and/or other variables the optimize plant growth and output. Specifically, the wave recipes may include a type of plants, and characteristics of different sound waves such as a frequency of audible sound, and a frequency of ultrasound. The wave recipes may correlate a type of different plants with different characteristics of sound waves. In some embodiments, the wave receipts may correlate the type of different plants with different combinations of sound waves having different characteristics. For example, wave recipes are shown in the table 1 below.

TABLE 1

| Wave recipes | | |
| --- | --- | --- |
| | Audible Sound | Ultrasound |
| Plant A | 500 Hz | 25,000 Hz |
| Plant B | No | 26,000 Hz |
| Plant C | 1,000 Hz | No |
| Plant D | 1,500 Hz | 30,000 Hz |

The master controller 106 instructs the wave generator 410 to output waves based on the wave recipes. The wave recipes correlate plants with different characteristics of waves, as shown in Table 1 above. The master controller 106 may identify the plants in the carts 104a through 104h, as plant A. For example, the master controller 106 may communicate with the carts 104 and receive information about the plants in the carts 104. Various sensors may be arranged in and around the assembly line grow pod 100. The master controller 106 may receive information from the sensors to identify plants in a particular cart 104. In some embodiments, the sensors may include a camera, a proximity sensor, a weight sensor, etc. For example, the camera takes an image of plants in the particular cart and sends to the master controller 106. As another example, the proximity sensor may detect plants in the particular cart and sends the information to the master controller. As another example, the information about the plants in the carts 104 may be pre-stored in the master controller 106 when the seeder component 108 seeds plant A in the carts 104. Specifically, the master controller 106 stores information associating the structure of the assembly line grow pod 100 with particular carts arranged at a particular location of the structure of the assembly line grow pod 100. In some embodiments, carts may have cart identifiers and once the cart identifiers are recognized, the master controller 106 may identify plants in the carts and the location of the carts.

Once the plants in the carts are identified, the master controller 106 instructs the wave generator 410 to generate waves of certain wavelengths based on wave recipes. For example, the master controller 106 determines that the carts 104 carry plant A. Then, the master controller 106 instructs the wave generator 410 to generate 500 Hz of audible sound and 25,000 Hz of ultrasound based on the wave recipe for plant A as shown in the Table 1 above. As another example, if the master controller 106 determines that the carts 104 carry plant B, the master controller 106 instructs the wave generator 410 to generate 26,000 Hz of ultrasound, but not to generate any audible sound based on the wave recipe for plant A as shown in the table 1 above.

The wave generator 410 may change the frequency of waves in real time according to the identification of plants being carried in the carts 104. For example, at time to, all the carts 104 carry plant A, and the wave generator 410 generates 500 Hz of audible sound and 25,000 Hz of ultrasound based on the wave recipe for plant A as shown in the table 1 above. At time t1, all the carts 104 are carrying plant C, and the wave generator 410 starts generating 1,000 Hz of audible sound based on the wave recipe for plant C as shown in the table 1 above. In some embodiments, prior to time t1, more than 50% of the carts 104 are carrying plant C, and the wave generator 410 starts generating 1,000 Hz of audible sound based on the wave recipe for plant C as shown in the table 1 above when more than 50% of the carts 104 are carrying plant C.

In some embodiments, the wave generator 410 may generate waves of changing frequencies based on the proportion of the plants in the assembly line grow pod 100. The proportion of the plants may indicate a percentage of a particular plant in the entire plants population. Based on the proportion of the plants, the wave generator 410 may generate waves having different characteristics corresponding to the proportion of the plants. A preset time may be set to generate waves by the wave generator 410 and the wave generator 410 may allot generation of a particular wave based on the proportion of the particular plant associated with, or correlated to the particular wave.

For example, if 50% of the carts 104 carry plant A, 30% of the carts 104 carry plant B, and 20% of carts 104 carry plant C at time t2, for a repeating period of a preset time period such as one minute, the wave generator 410 may generate 500 Hz of audible sound and 25,000 Hz of ultrasound for 30 seconds, 26,000 Hz of ultrasound for 18 seconds, and 1,000 Hz of audible sound for 12 seconds based on the wave recipes for plants A, B, and C as shown in Table 1. If 10% of the carts 104 carry plant A, 30% of the carts 104 carry plant B, and 60% of carts 104 carry plant C at time t3, for a repeating period of one minute, the wave generator 410 may generate 500 Hz of audible sound and 25,000 Hz of ultrasound for 6 seconds, 26,000 Hz of ultrasound for 18 seconds, and 1,000 Hz of audible sound for 36 seconds based on the wave recipes for plants A, B, and C as shown in the table 1. Any other time allocation of wave frequencies may be employed for the wave generator 410 based on identified plants in the assembly line grow pod 100. Additionally, or alternatively, the preset time period may vary based on various factors, such as a type of plants, growth patterns of plants, functions of the wave generator 410, characteristics of sound, the master recipe instructions, etc.

In embodiments, the wave recipes for plants may be updated based on information on harvested plants. For example, if the harvested plants A are generally smaller in size than an ideal plant A, the wave recipe for plant A may be updated to adjust the frequency of the ultrasound and/or the frequency of the audible sound.

It should also be understood that while the recipes described herein may include set frequencies, this is one example. In some embodiments, the recipes may be fluid to adjust based on growth of the plant, and/or other factors detected by the master controller 106.

Figure 3:
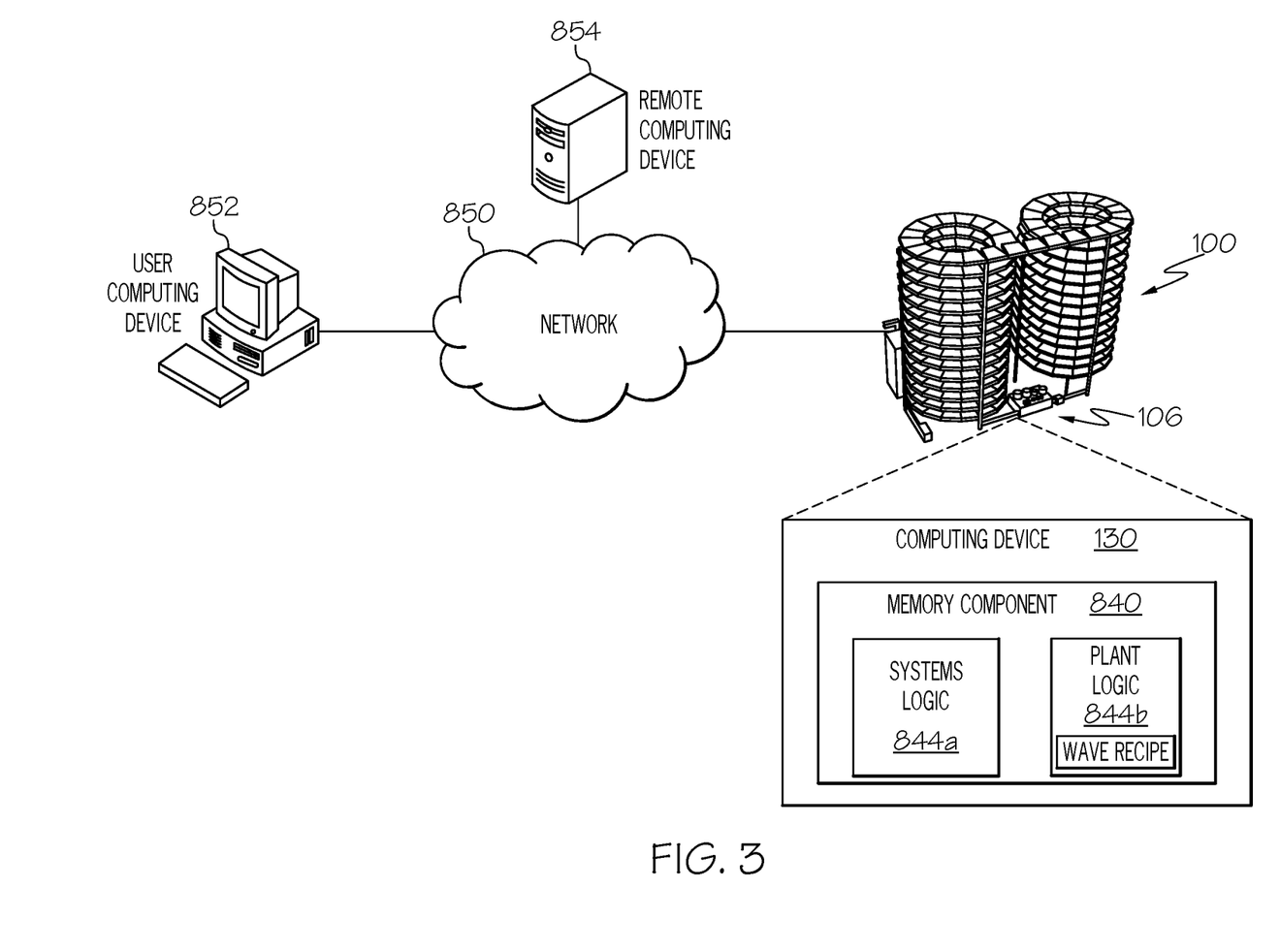
FIG. 3 depicts a computing environment for an assembly line grow pod, according to embodiments described herein.

FIG. 3 depicts a computing environment for an assembly line grow pod 100, according to embodiments described herein. As illustrated, the assembly line grow pod 100 may include a master controller 106, which may include a computing device 130. The computing device 130 may include a memory component 840, which stores systems logic 844a and plant logic 844b. As described in more detail below, the systems logic 844a may monitor and control operations of one or more of the components of the assembly line grow pod 100. For example, the systems logic 844a may monitor and control operations of the wave generator 410 The plant logic 844b may be configured to determine and/or receive a wave recipe for plant growth and may facilitate implementation of the recipe via the systems logic 844a For example, a recipe for, a plant determined by the plant logic 844b includes predetermined wave frequencies at predetermined times of plant development, and the systems logic 844a may instruct the wave generator 410 to generate waves of certain frequencies based on the wave recipes.

Additionally, the master controller 106 is coupled to a network 850. The network 850 may include the internet or other wide area network, a local network, such as a local area network, a near field network, such as Bluetooth or a near field communication (NFC) network. The wave generator 410 may be coupled to the network 850. The network 850 is also coupled to a user computing device 852 and/or a remote computing device 854. The user computing device 852 may include a personal computer, laptop, mobile device, tablet, server, etc. and may be utilized as an interface with a user. As an example, a user may send wave frequencies to the master controller 106 for implementation by the assembly line grow pod 100. A display of the user computing device 852 may display a frequency of wave generated by the wave generator 410 along with plants being grown in the assembly line grow pod 100.

Similarly, the remote computing device 854 may include a server, personal computer, tablet, mobile device, etc. and may be utilized for machine to machine communications. As an example, if the master controller 106 determines a type of seed being used (and/or other information, such as ambient conditions), the master controller 106 may communicate with the remote computing device 854 to retrieve a previously stored recipe for those conditions. As such, some embodiments may utilize an application program interface (API) to facilitate this or other computer-to-computer communications.

Figure 4:
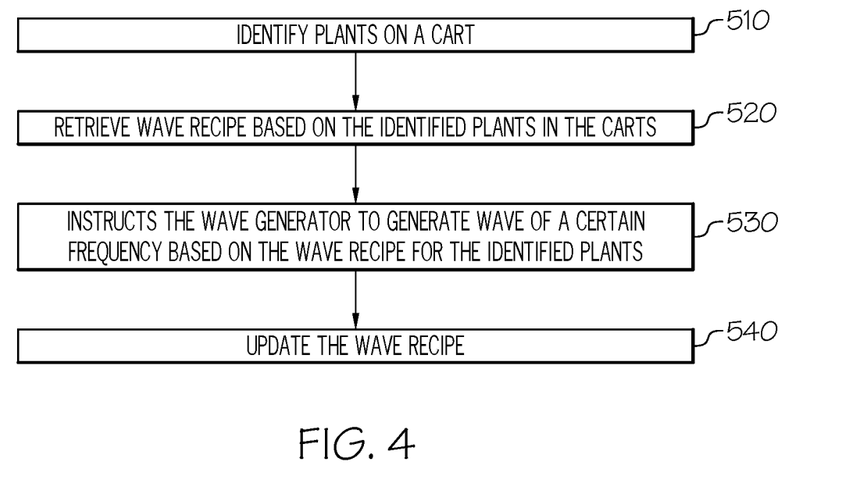
FIG. 4 depicts a flowchart for operating the wave generator based on the wave recipes, according to embodiments described herein.

FIG. 4 depicts a flowchart for operating the wave generator 410 based on the wave recipes, according to embodiments described herein. As illustrated in block 510, the master controller 106 identifies plants being carried in carts 104. For example, an operator inputs the type of seeds for plants that need to be grown in the carts through the user computing device 852, and the master controller 106 receives the type of seeds for plants from the user computing device 852. As another example, the master controller 106 may obtain identification of plants from the seeder component 108 that seeds the plants in the carts. As further another example, the master controller 106 may receive information from the sensors to identify plants in a particular cart 104. Additionally, or alternatively, the master controller 106 may detect a cart identifier of a cart carrying plants, which enables the master controller 106 to identify plants and corresponding wave recipes.

In block 520, the master controller 106 retrieves wave recipes based on the identified plants in the carts 104. In embodiments, the wave recipes may be pre-stored in the master controller 106. In some embodiments, the wave recipes may be stored in the remote computing device 854, and the master controller 106 retrieves the wave recipes from the remote computing device 854. In other embodiments, a user may input a particular wave recipe for a particular plant using a user computing device 852 via the network 850.

In block 530, the master controller 106 instructs the wave generator 410 to generate a certain frequency of ultrasound and/or a certain frequency of audible sound based on the wave recipes for the identified plants. As discussed above, in some embodiments, the master controller 106 instructs the wave generator 410 to generate low frequency (e.g. 500 Hz) of audible sound and high frequency (e.g. 25,000 Hz) of ultrasound based on the wave recipe for a particular plant, as shown in the table 1 above. As another example, the master controller 106 may instruct the wave generator 410 to generate only audible sound wave, or ultrasound wave. The wave generator 410 may change the frequency of waves, in real time, according to the identification of plants being carried in the carts 104. For example, as plant identifications may change, the wave generator 410 may generate waves customized to a plant identified in real time. Additionally, or alternatively, the wave generator 410 may generate a combination of waves having different ranges of frequency to cover different plants. In some embodiments, the combination of waves may be proportional to percentage of plants in a particular cart. For instance, if the particular cart carries 50% of Plant A and 50% of Plant B, the wave generator 410 may generate waves corresponding to Plant A and Plant B in combination.

In some embodiments, the wave generator 410 may generate waves of changing frequencies based on the portion of the plants in the assembly line grow pod 100. Then, the wave generator 410 may employ time allocation of wave frequencies based on proportions of the identified plants in the assembly line grow pod 100. For example, if 50% of the carts 104 carry plant A, 30% of the carts 104 carry plant B, and 20% of carts 104 carry plant C at time t2, for a repeating period of one minute, the wave generator 410 may generate 500 Hz of audible sound and 25,000 Hz of ultrasound for 30 seconds, 26,000 Hz of ultrasound for 18 seconds, and 1,000 Hz of audible sound for 12 seconds based on the wave recipes for plants A, B, and C as shown in the table 1. If 10% of the carts 104 carry plant A, 30% of the carts 104 carry plant B, and 60% of carts 104 carry plant C at time t3, for a repeating period of one minute, the wave generator 410 may generate 500 Hz of audible sound and 25,000 Hz of ultrasound for 6 seconds, 26,090 Hz of ultrasound for 18 seconds, and 1,000 Hz of audible sound for 36 seconds based on the wave recipes for plants A, B, and C as shown in the table 1.

In block 540, the mater controller 106 may update the wave recipes for plants based on information on harvested plants. For example, if the harvested plants A are generally smaller in size than an ideal plant A, the wave recipe for plant A may be updated to adjust the frequency of the ultrasound and/or the frequency of the audible sound.

Figure 5:
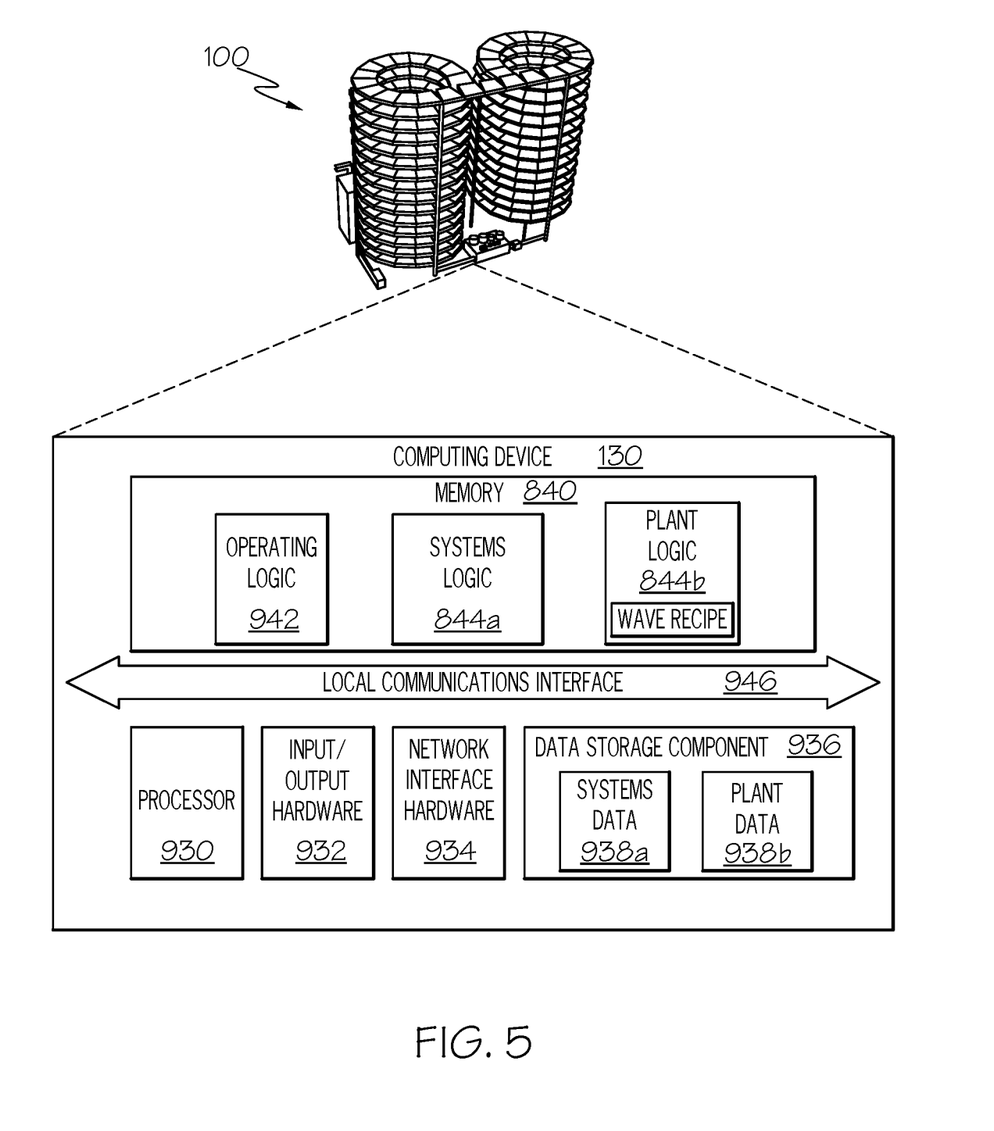
FIG. 5 depicts a computing device for an assembly line grow pod, according to embodiments described herein.

FIG. 5 depicts a computing device 130 for an assembly line grow pod 100, according to embodiments described herein. As shown in FIG. 3, the master controller 106 is implemented with the computing device 130. FIG. 5 further shows in detail various components of the computing device 130. In other embodiments, the computing device 130 may be configured to operate as a discrete control module that performs specific functions of controlling operations of the wave generator 410. More specifically, the master controller 106 is configured as a modular control interface and may delegate specific functions to different control modules. These control modules may be received into a plurality of bays with which the master controller 106 is equipped. These control modules may be removed from the bays for repair, reprogramming, upgrade, replacement, etc. without affecting or changing the operations of the master controller 106 and the remaining control modules.

As illustrated, the computing device 130 includes a processor 930, input/output hardware 932, the network interface hardware 934, a data storage component 936 (which stores systems data 938a, plant data 938b, and/or other data), and the memory component 840. The memory component 840 may be configured as volatile and/or nonvolatile memory and as such, may include random access memory (including SRAM. DRAM, and/or other types of RAM), flash memory, secure digital (SL)) memory, registers, compact discs (CD), digital versatile discs (DVD), and/or other types of non-transitory computer-readable mediums. Depending on the particular embodiment, these non-transitory computer-readable mediums may reside within the computing device 130 and/or external to the computing device 130.

The memory component 840 may store operating logic 942, the systems logic 844a, and the plant logic 844b. The systems logic 844a and the plant logic 844b may each include a plurality of different pieces of logic, each of which may be embodied as a computer program, firmware, and/or hardware, as an example. A local interface 946 is also included in FIG. 5 and may be implemented as a bus or other communication interface to facilitate communication among the components of the computing device 130.

The processor 930 may include any processing component operable to receive and execute instructions (such as from a data storage component 936 and/or the memory component 840). The input/output hardware 932 may include and/or be configured to interface with microphones, speakers, a display, and/or other hardware.

The network interface hardware 934 may include and/or be configured for communicating with any wired or wireless networking hardware, including an antenna, a modem, LAN port, wireless fidelity (Wi-Fi) card, WiMax card, ZigBee card, Bluetooth chip, USB card, mobile communications hardware, and/or other hardware for communicating with other networks and/or devices. From this connection, communication may be facilitated between the computing device 130 and other computing devices, such as the user computing device 852 and/or remote computing device 854.

The operating logic 942 may include an operating system and/or other software for managing components of the computing device 130. As also discussed above, systems logic 844a and the plant logic 844b may reside in the memory component 840 and may be configured to perform the functionality, as described herein.

It should be understood that while the components in FIG. 5 are illustrated as residing within the computing device 130, this is merely an example. In some embodiments, one or more of the components may reside external to the computing device 130. It should also be understood that, while the computing device 130 is illustrated as a single device, this is also merely an example. In some embodiments, the systems logic 844a and the plant logic 844b may reside on different computing devices. As an example, one or more of the functionalities and/or components described herein may be provided by the user computing device 852 and/or remote computing device 854.

Additionally, while the computing device 130 is illustrated with the systems logic 844a and the plant logic 844b as separate logical components, this is also an example in some embodiments, a single piece of logic (and/or or several linked modules) may cause the computing device 130 to provide the described functionality.

As illustrated above, various embodiments for utilizing waves in a grow pod are disclosed. These embodiments create a quick growing, small footprint, chemical free, low labor solution to growing microgreens and other plants for harvesting. These embodiments may create recipes and/or receive recipes that dictate the timing and wavelength of light, pressure, temperature, watering, nutrients, molecular atmosphere, and/or other variables the optimize plant growth and output. The recipe may be implemented strictly and/or modified based on results of a particular plant, tray, or crop.

Accordingly, some embodiments may include a grow pod that includes a cart that holds at least one plant and/or seed; a wave generator configured to generate waves; and a master controller configured to identify the at least one plant in the cart; retrieve wave recipes based on the identified plants; and instruct the wave generator to generate the waves at certain frequencies based on the wave recipes, wherein the wave recipes include frequencies of ultrasound and frequencies of audible sound. As illustrated above, various embodiments for utilizing waves in the assembly line grow pod are disclosed. In these embodiments, the waves may be utilized to promote and maximize growth of plants supported by the assembly line grow pod. Accordingly, waves have been generated and provided based on wave recipe that store plants specific wave information. Wave recipe may be prepared and stored in the master controller and as plants grow and users send input relating to the wave recipe, the wave recipe is updated and modified as needed.

As discussed in the embodiments described above, a method for utilizing waves in an assembly line grow pod includes (i) arranging a plurality of plants having a first plant and a second plant on a plurality of carts; (ii) identifying the first plant carried on one or more carts; (iii) identifying the second plant carried on one or more carts; (iv) storing, in a memory, a wave recipe that correlates the plants on the carts with different characteristics of sound waves; (v) upon identification of the first plant, retrieving from the wave recipe a characteristic of the sound wave correlated to the first plant; (vi) upon identification of the second plant, retrieving from the wave recipe a characteristic of the sound wave correlated to the second plant; (v) generating, with a wave generator, a first sound wave having the characteristic correlated to the first plant; and (vii) generating, with the wave generator, a second sound wave having the characteristic correlated to the second plant.

In some embodiments, the step of generating the first sound wave further includes generating the first sound wave having a first frequency correlated to the first plant, and generating the second sound wave further comprises generating the second sound wave having a second frequency correlated to the second plant. The step of generating the second sound wave further includes: upon identification of the second plant, generating, in real time, the second sound wave having the characteristic correlated to the second plant.

In another embodiment, the method for utilizing waves in the assembly line grow pod further includes determining whether a proportion of the first plant among the plurality of plants is higher than a predetermined threshold; and upon determination that the proportion of the first plant is higher than the predetermined threshold, generating the first sound wave having the characteristic correlated to the first plant.

In another embodiment, the method for utilizing waves in the assembly line grow pod further includes determining a first proportion of the first plant among the plurality of plants; and determining a second proportion of the second plant among the plurality of plants. The step of generating the first sound wave further includes generating the first sound wave during a first time period allocated corresponding to the first proportion of the first plant out of a preset time, and the step of generating the second sound wave further includes generating the second sound wave during a second time period allocated corresponding to the second proportion of the second plant out of the preset time. The method for utilizing waves further includes updating the wave recipe based on growth pattern of the first plant, the second plant, or both. The method for utilizing waves further includes that the step of generating the first sound wave further includes generating the first sound wave having audible sound and the step of generating the second sound wave further includes generating a ultrasound wave.

In another embodiment, the method for utilizing waves in the assembly line grow pod further includes determining each proportion of the carts carrying the first plant and the carts carrying the second plant. The step of generating the first sound wave further includes generating the first sound wave during a third time period in proportion to a proportion of the carts carrying the first plant, out of a preset time; and generating the second sound wave further includes generating the second sound wave during a fourth time period in proportion to a proportion of the carts carrying the second plant, out of a preset time. The step of determining each proportion of the carts further includes determining a proportion of the carts carrying the first plant among the entire carts carrying the plurality of plants. The step of generating the first sound wave further includes generating the first sound wave during the third time period in proportion to the proportion of the carts carrying the first plant, upon determination that the proportion of the carts carrying the first plant exceeds a predetermined threshold.

In another embodiment, the method for utilizing waves in the assembly line grow pod further includes determining a proportion of the carts carrying the first plant among the entire carts carrying the plurality of plants. The step of generating the first sound wave further includes: upon determination that the proportion of the carts carrying the first plant exceeds a predetermined threshold, generating the first sound wave. The step of generating the first sound wave further includes generating both audible sound and an ultrasound wave. Alternatively, or additionally, the step of generating the second sound wave further includes generating the second sound wave including audible sound and no ultrasound wave.

In another embodiment, the method for utilizing waves in the assembly line grow pod further includes (i) determining each proportion of the carts carrying the first plant and the carts carrying the second plant at a first timing (t1), respectively; (ii) generating the first sound wave and the second sound wave in proportion to each proportion, at the first timing (t1), of the carts carrying the first plant and the second plant; (iii) determining each different proportion of the carts carrying the first plant and carrying the second plant at a second timing (t2), respectively; and (iv) generating the first sound wave and the second sound wave in proportion to each proportion, at the second timing (t2), of the carts carrying the first plant and the second plant.

In another embodiment, the method for utilizing waves in the assembly line grow pod further includes (i) receiving an input relating to the wave recipe from a remote computer via network; (ii) storing the input relating to the wave recipe in the memory, and (iii) updating, with the master controller, the wave recipe based on growth patterns of the first plant, the second plant, or both. The step of identifying the first plant carried on the carts further includes identifying one or more cart identifiers of the carts carrying the first plant.

The wave generator generates customized and selected waves having a different range of frequency and wavelength based on the wave recipe. The master controller controls operations of the wave generator to reflect the actual conditions of the assembly line grow pod. For example, if a particular type of plant is a majority of plants supported by the assembly line grow pod, waves relevant to the particular type of plant may be provided for a longer period of time. The master controller may identify percentages of multiple plants by determining percentages of carts carrying each plant. The master controller controls the wave generator to allow time for generating and providing waves corresponding to each percentage of carts carrying the multiple plants.

The wave generator generates sound waves which range a wide range of frequency. The sound waves include audible sound, ultrasound, etc. based on plants supported by the assembly line grow pod identification of plants may be performed using various mechanisms. The master controller may identify each cart identifier which indicates information of plants carried on a particular cart. Various sensors may be arranged in and around the assembly line grow pod to provide identification information of plants to the master controller. Growth of plants may be customized and optimized by using waves relevant to a type and population of plants.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for utilizing waves in an assembly line grow pod. It should also be understood that these embodiments are merely exemplary and are not intended to limit the scope of this disclosure.

What is claimed is:

1. A method for utilizing waves in an assembly line grow pod, comprising:
    arranging a plurality of plants having a first plant and a second plant on a plurality of carts;
    identifying the first plant carried on a first cart of the plurality of carts;
    identifying the second plant carried on a second cart of the plurality of carts;
    storing, in a memory, a wave recipe that correlates the plants on the plurality of carts with different characteristics of sound waves;
    upon identification of the first plant, retrieving from the wave recipe a first sound wave characteristic that is correlated to the first plant;
    upon identification of the second plant, retrieving from the wave recipe a second sound wave characteristic that is correlated to the second plant;
    generating, with a wave generator, a first sound wave having the first sound wave characteristic that is correlated to the first plant; and
    generating, with the wave generator, a second sound wave having the second sound wave characteristic that is correlated to the second plant.

2. The method of claim 1, wherein generating the first sound wave further comprises generating the first sound wave having a first frequency correlated to the first plant; and
    generating the second sound wave further comprises generating the second sound wave having a second frequency correlated to the second plant.

3. The method of claim 1, wherein generating the second sound wave further comprises: upon identification of the second plant, generating, in real time, the second sound wave having the characteristic correlated to the second plant.

4. The method of claim 1, further comprising:
    determining whether a proportion of the first plant among the plurality of plants is higher than a predetermined threshold;
    wherein generating the first sound wave further comprises: upon determination that the proportion of the first plant is higher than the predetermined threshold, generating the first sound wave having the characteristic correlated to the first plant.

5. The method of claim 1, further comprising:
    determining a first proportion of the first plant among the plurality of plants; and
    determining a second proportion of the second plant among the plurality of plants;
    wherein generating the first sound wave further comprises generating the first sound wave during a first time period allocated corresponding to the first proportion of the first plant out of a preset time; and
    generating the second sound wave further comprises generating the second sound wave during a second time period allocated corresponding to the second proportion of the second plant out of the preset time.

6. The method of claim 1, further comprising updating the wave recipe based on growth pattern of the first plant, the second plant, or both.

7. The method of claim 1, wherein generating the first sound wave further comprises generating audible sound and an ultrasound wave.

8. The method of claim 1, further comprising:
    determining a first proportion of the plurality of carts carrying a first type of plant that is similar to the first plant and a second proportion of the plurality of carts carrying a second type of plant that is similar to the second plant;
    wherein generating the first sound wave further comprises generating the first sound wave during a third time period in proportion to the first proportion of the plurality of carts carrying the first type of plant, out of a preset time; and
    generating the second sound wave further comprises generating the second sound wave during a fourth time period in proportion to the second proportion of the plurality of carts carrying the second type of plant, out of a preset time.

9. The method of claim 8, wherein determining the first proportion of the plurality of carts further comprises determining a third proportion of the plurality of carts carrying the first type of plant among all carts carrying the plurality of plants; and
    wherein generating the first sound wave further comprises generating the first sound wave during the third time period in proportion to the third proportion, upon determination that the third proportion exceeds a predetermined threshold.

10. The method of claim 1, further comprising:
determining a proportion of the plurality of carts carrying the first type of plant among the plurality of carts carrying the all of the plurality of plants; and
wherein generating the first sound wave further comprises: upon determination that the proportion of the carts carrying a type of plant that is similar to the first plant exceeds a predetermined threshold, generating the first sound wave.

11. The method of claim 1, further comprising:
determining a first proportion of the plurality of carts carrying a type of plant that is similar to the first plant and a second proportion of the plurality of carts carrying the second plant at a first timing (t1), respectively;
generating the first sound wave and the second sound wave in proportion to each of the first proportion and the second proportion, at the first timing (t1), of the plurality of carts carrying the first type of plant and the second type of plant;
determining the first proportion and the second proportion at a second timing (t2), respectively; and
generating the first sound wave and the second sound wave in proportion to each of the first proportion and the second proportion, at the second timing (t2), of the plurality of carts carrying the first type of plant and the second type of plant.

12. A method for utilizing waves in an assembly line grow pod, comprising:
receiving a plurality of plants having a first plant and a second plant on a plurality of carts;
storing, in a memory of a master controller, a wave recipe that correlates the plants on the carts with a characteristic of sound waves;
controlling, with the master controller, a wave generator to generate sound waves having different characteristics based on the wave recipe;
identifying, with the master controller, the first plant carried on the carts;
identifying, with the master controller, the second plant carried on the carts;
upon identification of the first plant, retrieving from the wave recipe the characteristic of the sound waves correlated to the first plant;
upon identification of the second plant, retrieving from the wave recipe the characteristic of the sound waves correlated to the second plant;
generating, with the wave generator, a first sound wave having the characteristic correlated to the first plant; and
generating, with the wave generator, a second sound wave having the characteristic correlated to the second plant.

13. The method of claim 12, further comprising:
receiving an input relating to the wave recipe from a remote computer via network;
storing the input relating to the wave recipe in the memory; and
updating, with the master controller, the wave recipe based on growth patterns of the first plant, the second plant, or both.

14. The method of claim 12, wherein identifying the first plant carried on the carts further comprises identifying one or more cart identifiers of the carts carrying the first plant.

15. A system for utilizing waves in an assembly line grow pod, comprising:
a plurality of carts carrying a plurality of plants including a first plant and a second plant;
a wave generator that generates sound waves having a different range of a frequency; and
a master controller communicatively coupled to the wave generator and comprising a processor and a memory storing a wave recipe and instructions, wherein the wave recipe correlates the plurality of plants with different characteristics of sound waves, and the instructions, upon execution by the processor, perform operations comprising:
identifying the first plant carried on the carts;
identifying the second plant carried on the carts;
retrieving from the wave recipe each characteristic of the sound waves of the first plant and the second plant, respectively;
causing the wave generator to generate a first sound wave having the characteristic correlated to the first plant; and
causing the wave generator to generate a second sound wave having the characteristic correlated to the second plant.

16. The system of claim 15, wherein upon execution by the processor, the instructions cause the wave generator to:
generate the first sound wave having a first frequency; and
generate the second sound wave having a second frequency, which is higher than the first frequency.

17. The system of claim 15, wherein upon execution by the processor, the instructions perform operations further comprising:
identifying a proportion of the first plant among the plurality of plants;
identifying a proportion of the second plant among the plurality of plants;
causing the wave generator to generate the first sound wave during a first time period in proportion to the proportion of the first plant, out of a preset time period; and
causing the wave generator to generate the second sound wave during a second time period in proportion to the proportion of the second plant, out of the preset time period.

18. The system of claim 15, wherein upon execution by the processor, the instructions perform operations further comprising:
identifying a proportion of the first plant among the plurality of plants; and
causing the wave generator to generate the first sound wave when the proportion of the first plant exceeds a majority of the plurality of plants.

19. The system of claim 15, wherein upon execution by the processor, the instructions perform operations further comprising:
identifying the first plant;
causing the wave generator to generate the first sound wave having a first frequency;
subsequently identify the second plant; and
causing the wave generator to generate the second sound wave having a second frequency in real time.

20. The system of claim 15, wherein upon execution by the processor, the instructions perform operations further comprising:
causing the wave generator to generate the second sound wave including audible sound and no ultrasound wave.

* * * * *